United States Patent [19]
Larrabee et al.

[11] 4,043,501
[45] Aug. 23, 1977

[54] PORTABLE LIQUID PACKAGE CONTAINER FOR USE WITH BLOOD WASHING DEVICE

[75] Inventors: Edward Whittum Larrabee, Bronxville, N.Y.; Paul Olney Rawson, Easton; Richard Hajime Yagami, Westport, both of Conn.

[73] Assignee: Union Carbide Corporation, New York, N.Y.

[21] Appl. No.: 737,605

[22] Filed: Nov. 1, 1976

[51] Int. Cl.² .............................................. B65D 5/40
[52] U.S. Cl. ................................ 229/14 BE; 222/129
[58] Field of Search ......................... 229/14 B, 14 BE; 222/129, 130, 183

[56] References Cited
U.S. PATENT DOCUMENTS

| | | | |
|---|---|---|---|
| 2,039,684 | 5/1936 | Dudley | 222/130 |
| 3,089,622 | 5/1963 | Westlake, Jr. | 229/14 B |
| 3,352,472 | 11/1967 | Cummings et al. | 229/14 B |

FOREIGN PATENT DOCUMENTS 1,207,421  9/1970  United Kingdom ............ 229/14 BE Primary Examiner—Davis T. Moorhead
Attorney, Agent, or Firm—Frederick J. McCarthy, Jr.

[57] ABSTRACT

Portable liquid package container arrangement for use with blood washing device.

1 Claim, 9 Drawing Figures

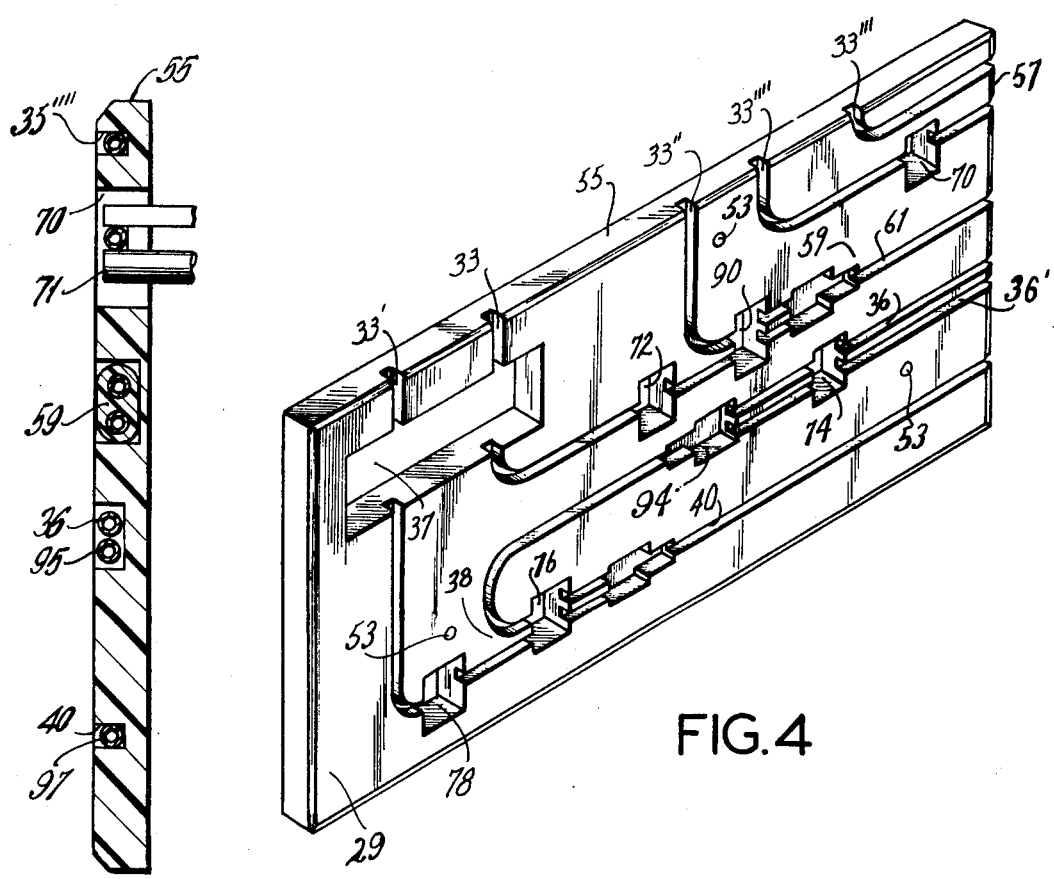
FIG.3
FIG.4
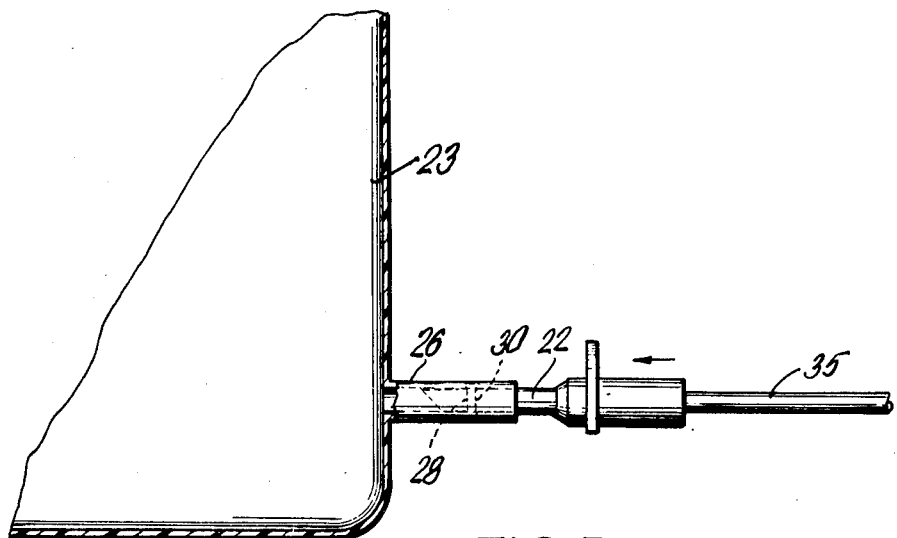
FIG.5

PORTABLE LIQUID PACKAGE CONTAINER FOR USE WITH BLOOD WASHING DEVICE

The present invention relates to blood washing apparatus and more particularly to a portable liquid package container arrangement for use with a blood washing apparatus.

Blood washing is a procedure known to the art, for example, as described in U.S. Pat. No. 3,982,691 — Centrifuge Separation and Washing Device and Method — Charles A. Schlutz, issued Sept. 28, 1976. As described in the above-noted United States patent human blood from volunteer donors is washed to remove unwanted constituents such as contaminants, toxicants, viruses, medicants, glycerines, cellular debris and the like, using a device based on centrifugal separation. Such a device includes a rotatable enclosure into which liquids, such as blood and wash liquids, e.g. saline solutions are injected, and from which the washed blood, wash liquids and unwanted constituents are removed. While the device described in the above-noted patent can be used to wash blood continuously, in a particular mode of operation, a predetermined amount of blood, e.g. a package available from a blood banking organization, is washed using predetermined packaged quantities of wash solution. Under such circumstances it is desirable to provide a portable liquid package container arrangement for the supply of saline solutions and recovery of washed blood and waste liquid.

It is therefore an object of the present invention to provide for use with a blood washing device a portable liquid package container for the supply of saline solutions and recovery of washed blood and waste liquid.

Other objects will be apparent from the following description and claims taken in conjunction with the drawing wherein FIG. 1 shows somewhat schematically a blood washing device FIG. 2, 2(a), 2(b), 3, 4 and 5 show a tubing harness arrangement and details thereof for use with the blood washing device of FIG. 1

Figure 1:
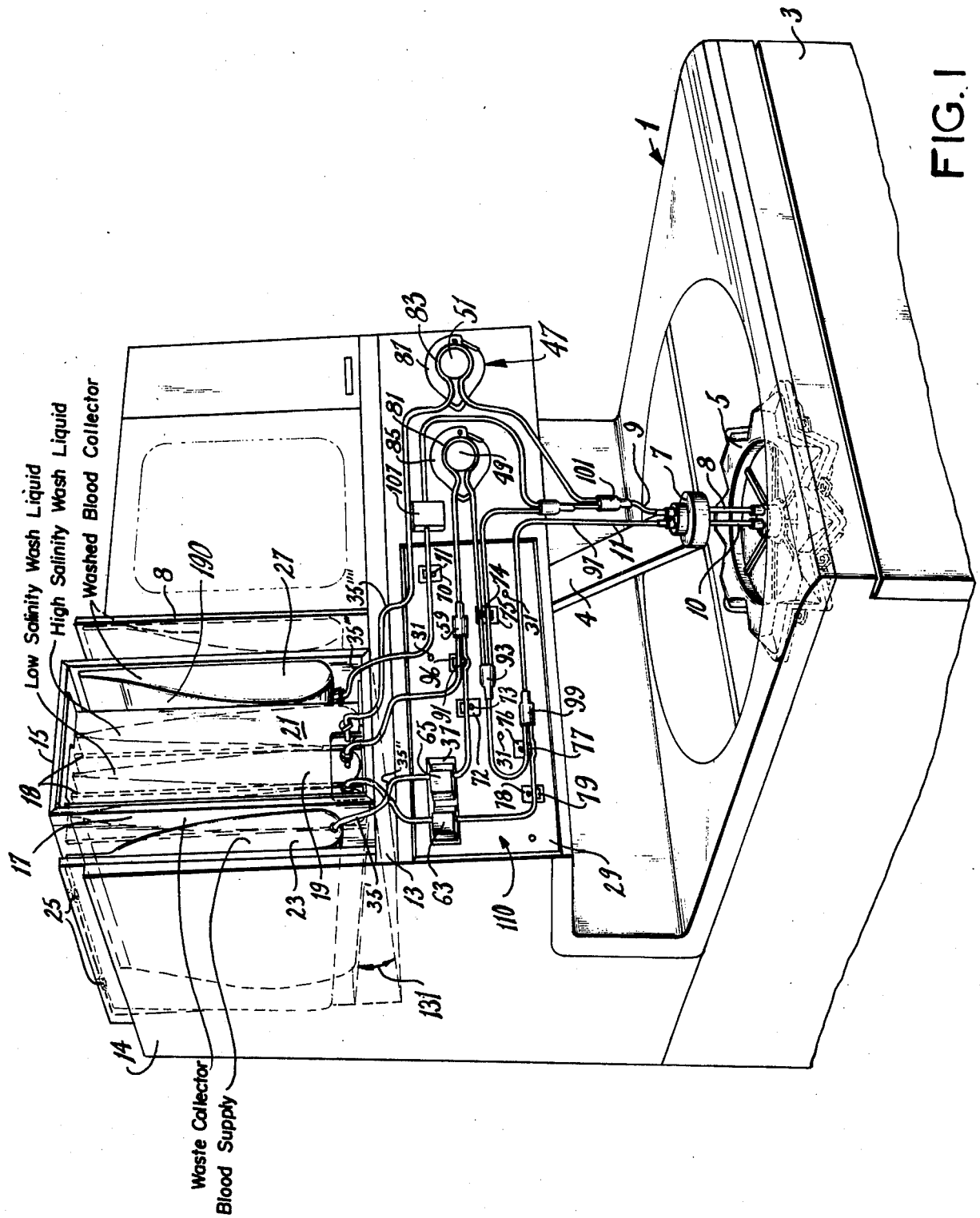

With reference to FIG. 1 of the drawing, a blood washing apparatus is indicated at 1 having an enclosing housing 3 in which is contained a rotatable enclosure means 5 such as the type described in the above-noted U.S. Pat. No. 3,982,691 which washes blood cells in the manner described in the patent.

A fluid connector 7, supported on arm 4 above entry conduit 8 and exit conduit 10 provides fluid communication with blood washing enclosure means 5. Fluid connector 7 has two conduits 9 and 11 for the entry and removal of liquid as hereinafter described.

Housing member 3 is provided with a shelf member 13 and side supports 14 and 8 which supports a corrugated cardboard container 15, having partitions 18, e.g. mad of cardboard, which supportably holds an initially empty liquid waste package 17, an initially loaded low concentration saline solution containing package 19, and an initially loaded high concentration saline solution containing package 21. A blood containing package 23, such as a package obtained from a blood bank, is supported by means of hooks on side support 14 as indicated at 25.

An initially empty blood collection package 27 is supportably positioned within open-front compartment 190 of container 15 and during blood washing is supported on side support 8 in a manner similar to package 23. The above-described packages 17, 19, 21, 23 and 27 are suitably made of a collapsible transparent flexible plastic material such as polyolefins, polyvinyl chloride and the like.

The horizontally disposed array of adjacent packages 17, 19, 21, 23 and 27 located in container 15 are located above a disposable tubing harness arrangement 110 which is described in co-pending patent application "Disposable Tubing Harness for Use with Blood Washing Apparatus". As described in the above-mentioned patent application, the disclosure of which is incorporated herein by reference, a board-like member 29 is removably engaged to housing 3 by support pins as indicated at 31. Board-like member 29 is suitably made of polyvinyl chloride or polyurethane and the like and contains grooves 33, 33', etc., as particularly indicated in FIG. 2 which respectively engage and securely hold flexible tubes 35, 35', etc., which are transparent and also suitably made of polyvinyl chloride polyurethane and the like. Board-like member 29 also has openings as hereinafter described to provide clearance for valves and sensors which are mounted on housing 3 and which receive electrical signals from or provide electrical signals to a conventional electrical control unit (not shown) which is contained within housing 3. Housing 3 also contains conventional peristaltic pumps 45 and 47 which have motor driven shaft extensions 49 and 51 respectively which have cross-sections lying in substantially the same vertical plane as the grooves 33, 33', etc., of board-like member 29. The rotation of the shafts 49 and 51 of pumps 45 and 47 may be conventionally controlled by singals from a control unit (not shown).

Figures 2, 2A, 2B:
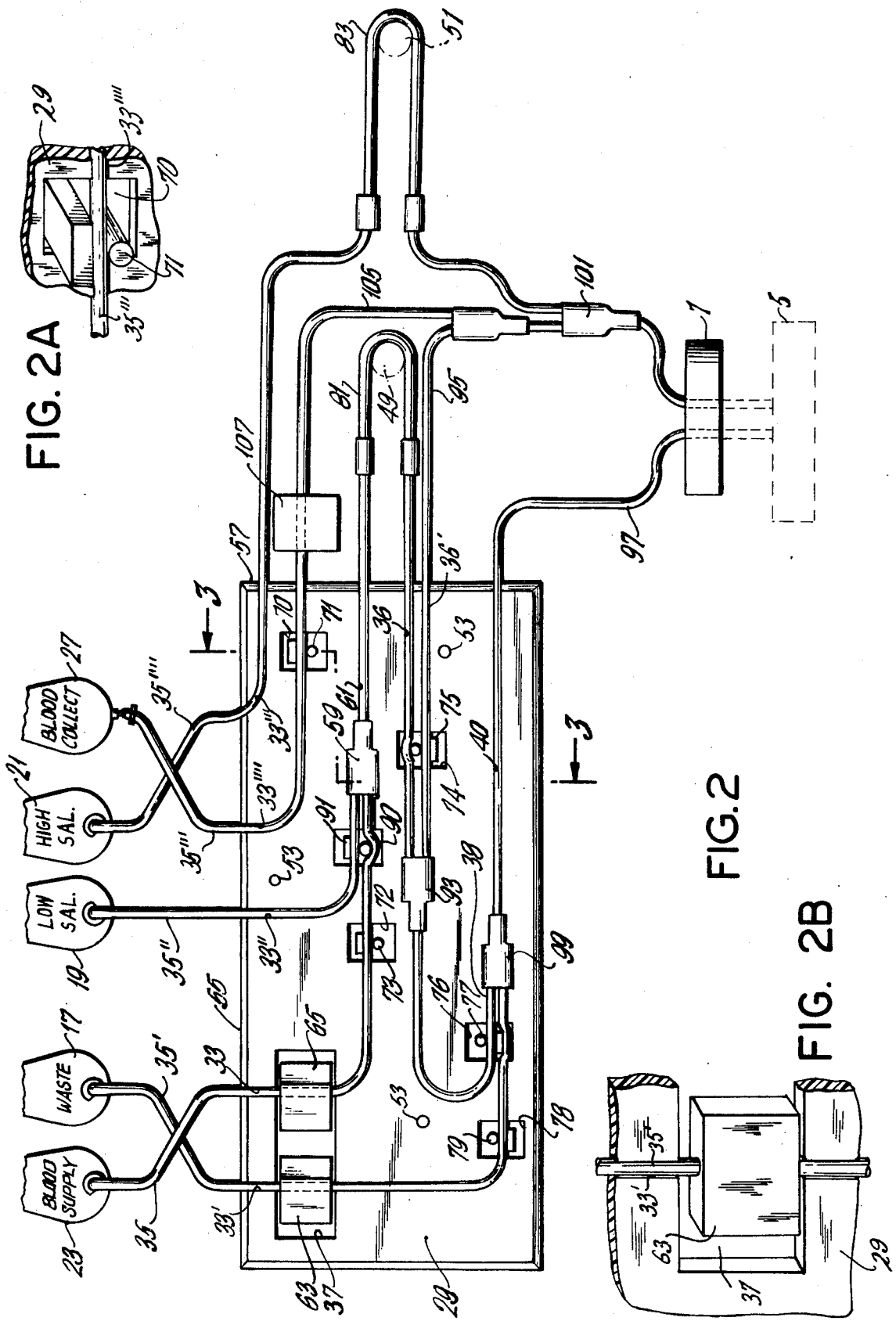

With reference to FIGS. 2, 3 and 4, packages 17, 19, 21, 23 and 27 are connected to flexible tubes 35—35'''' for example by means of a "Spike" connector arrangement as shown in FIG. 5 comprising a pointed extension member 22 which is force fitted by hand in conduit extension 26 and pierces a plastic membrane 30.

Board-like member 29 is mounted on pin arrangement 31 on housing 3 by means of holes 53 in board-like member 29. Each of the flexible conduits 35—35'''' is force fitted into a groove 33—33'''' which extends from the upper edge 55 of board-like member 29 to the side 57 of board-like member 29 which is adjacent the horizontally disposed peristaltic pump shafts 49 and 51 is shown in FIG. 1. An additional groove 36 extends from side 57 into the interior of board-like member 29 to join with groove 33' at 38 into a single groove 40. A further additional groove 39 extends parallel to groove 36 and joins groove 36 and 94. As shown in FIG. 2, grooves 33 and 33'' joint at 59 into a single groove 61. Board like member 29 is provided withopenings at locations along various groove paths to accommodate optical sensors 63 and 65, in opening 37, and pinch valves 71, 73, 75, 77, 79 and 91 in openings 70, 72, 74, 76, 78 and 90 respectively. The above noted optical sensors and pinch valves are mounted on housing 3 and are electrically connected to conventional control unit (not shown).

With the flexible tubes 35—35'''' assembled in board-like member 29 and the tubes connected to packages 17, 19, 21, 23 and 27 as shown in FIG. 1, loops 81 and 83 are fitted around peristaltic pump shafts 49 and 51 as also shown in FIG. 1 and held fixed with respect to the shafts by clamps 85 and 87 as shown in FIG. 1.

With the tube harness arrangement of the present invention in place as described above, the blood washing apparatus shown in FIG. 1 can be operated. For example, low concentration saline solution from package 19 is pumped by the rotation of peristaltic pump shaft 49 through tube 35" to T connection 59, valve 91 being open, to T connection 93 where flow is reversed, due to valve 77 being closed and valve 75 being open, whereby low concentration saline solution passes through tube section 95 via connector 7 into rotating enclosure member 5, thereby priming enclosure member 5. Low saline solution in excess of that required for priming exits enclosure member 5 via connector 7 and tube section 97 through T connection 99 and tube 35' to waste package 17. After priming with low concentration saline solution valve 73 is opened and, blood from package 23 is pumped via tube 35 into enclosure member 5 by the same path as the previously described low concentration saline solution prime. Optical sensor 65 detects the start and finish of blood flow through transparent tube 35 and at the finish provide an electrical signal to control unit 43, shown in FIG. 1, so that signals can be provided to the valves and pumps in the following "wash" step.

Figure 6:
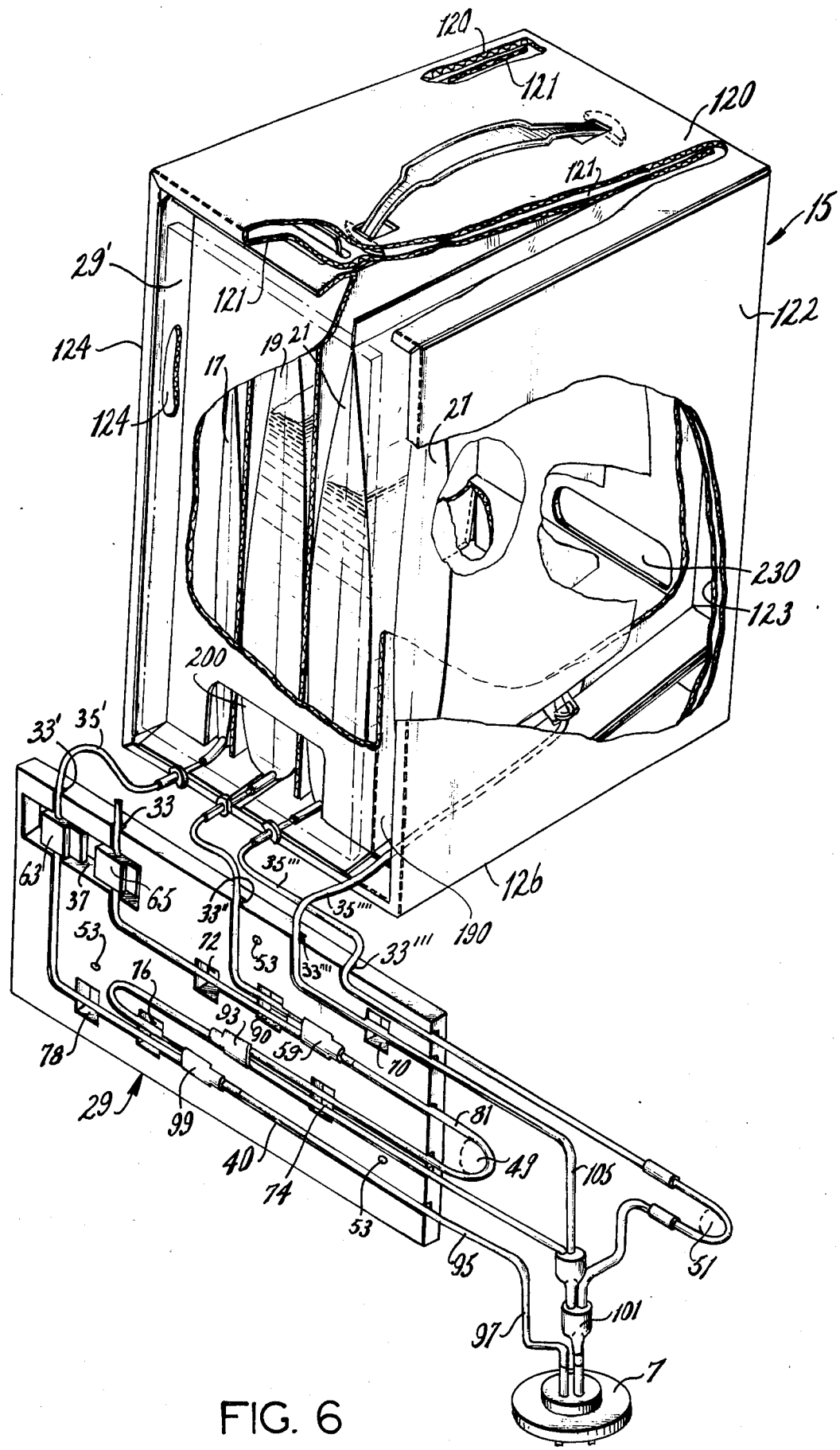
FIG. 6 shows the portable package arrangement of the present invention.
Figure 7:
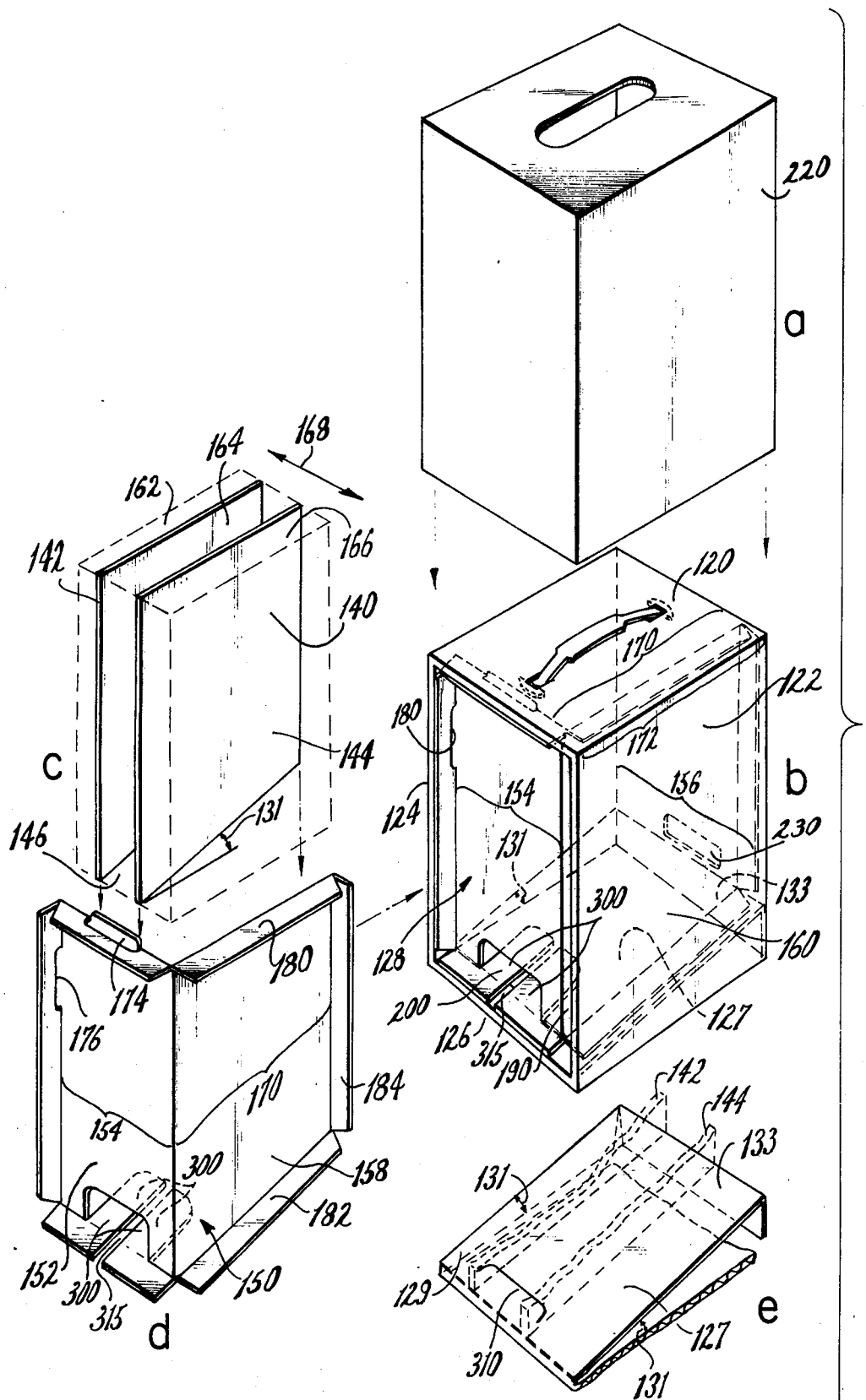
FIG. 7 shows details of the portable package of FIG. 6

In the wash step, pump shafts 49 and 51 can be both operated to provide a continuous flow saline solution of predetermined relatively high concentration into enclosure member 5, the higher saline concentration solution proceeding directly from package 21 via flexible tube 35"" through T connection 101 and connector 7 to enclosure member 5; the low concentration saline solution proceeds from package 19 in the same manner as the above described priming step. During the washing step, saline solution containing contaminants, etc., i.e. waste liquid, is continuously removed from enclosure member 5 to waste package 17 in the same manner as excess saline solution was removed in the above described priming step. When the predetermined washing period is over, the washed blood is collected from enclosure member 5 into package 27 by the action of pump shaft 49 which pumps low concentration saline solution from package 19 into enclosure member 5 by way of tube 35", open valve 91 T connection 59, tubes 81 and 36, T connection 93, open valve 77, T connection 99 and tube 97. The washed blood is forced to exit through T connection 101 tube 105, open valve 71 and tube 35'" to blood collection package 27. During the foregoing collection step valves 79 and 75 are closed and pump 50 is deactuated. The passage of washed blood is detected by optical sensor 107 and when blood is no longer detected the pump shaft 49 is stopped by a signal from a conventional control unit. Optical sensor 63 monitors the flow of waste liquid into waste collection package 17. The portable liquid package arrangement of the present invention indicated at 15 in FIG. 1 is especially configured to be used in combination with the blood washing device as aforedescribed.

with reference to FIG. 6, an integral corrugated cardboard support member 15 is enclosed at its top 120, sides 122 and 124 and bottom 126 and is initially open at its front 128 as shown more clearly in FIG. 7(b). The top 120 of corrugated cardboard support member 15 has a top extension member 121 which is integral therewith and is folded back into support member 15 to fit tightly therein adjointly below and parallel the top 120 and provides a cushioning double layer of corrugated cardboard. Similarly, side 122 of support member 16 has a side extension member 123 which is integral therewith and is folded back into support member 15 to fit tightly therein adjacently parallel to side 122 and also provides a cushioning double layer of corrugated cardboard. In the same manner, side 124 of support member 15 has a side extension member 125 which is integral therewith and is folded back into support member 15 to fit tightly therein adjacently parallel to side 124 and provides a cushioning double layer of corrugated cardboard. Bottom 126 of support member 15 has a bottom extension member 127, is also shown in FIG. 7(e), which is integral therewith and is folded back into support member 15 to fit tightly therein; bottom extension member 127 has a folded down side portion 129 in contact with the bottom 126 of support member 15 which is at a small acute angle 131. Bottom extension member 127 is thus at a slope with respect to the horizontal so that when positioned on sloped shelf member 13, shown in FIG. 1, the bottom extension member 127 will in fact be horizontal, while support member 15 securely rests on sloped shelf 13 which is attached to sloped back support member 14 as shown in FIG. 1. Folded down end portion 133 of bottom extension member 127 rests on bottom 126 of support member 15 to align and firmly support bottom extension member 127 at 10 on bottom 126 of support member 15.

A pair of removable vertical partitions 140 and 142, as also shown in FIG. 7(c), e.g. made of corrugated cardboard are supported along their lower edges 144 and 146 on bottom extension member 127, the edges 144 and 146 being slanted at the same small acute angle 131 as the bottom extension member 127.

A front closure member 150 formed of corrugated cardboard has a vertical front portion 152 having a width 154 which is a predetermined distance less than the width 156 of support member 15. Front closure member 15 has an integral side portion 158 which is folded into support member 15 to form therein an enclosed compartment 160 within which vertical partitions 140 and 142 form three vertical sections 162, 164 and 166 within which liquid receptacles 17, 19 and 21 are arranged. Partitions 140 and 142 are loosely fitted in enclosed compartment 160 and are slidably movable laterally as indicated at 168 to accommodate the expansion of liquid package 17 upon the filling thereof with waste liquid, the volume expansion being compensated by the removal of saline from packages 19 and 21 during blood washing as hereinabove described.

As shown in FIG. 7(c) front closure member 152 has a depth 170 which is less than the depth 172 of support member 15 and hence is recessed a predetermined distance within enclosure member 15. In the recessed position, integral tabs 174 and 176 engage with slots 178 and 180 in top extension member 121 and side extension member 123. Tabs 300 of front closure member 152 engage slot 310 of bottom extension member 127; slot 315 permits the passage of the tubes 33, 33' and 33" of pre-inserted packages 17, 19 and 21 upon installation of front closure member 152. Front closure member 152 has folded over integral edge member 180, 182 and 184 of the same predetermined width which provides a snug fit of front closure member 152 in support member 15 and establishes an open compartment 190 within which blood collecting package 27 is located. Front closure member 152 has an aperture 200 at its lowermost edge through which, as shown, in FIG. 6 tubes 33', 33" and 33'" can be connected to packages 17, 19 and 21, e.g. in the manner indicated in FIG. 5. Tubes 33', 33", etc., are engaged in board like member 29. Board-like member 29 is sized to fit in the recessed front portion of support member 15 as indicated at 29', the connections to fluid connector 7 being removed under such circumstances. A closure member 220 slides over support member 15 and the assembled container arrangement can be carried by strap 225 which is affixed to support member 15. An additional aperture 230 is provided at the lower rear portion of support member 15 so that the condition of the packages 19 and 21 can observed by viewing through apertures 200 and 230.

The portable container arrangement of the present invention is assembled by laying support member 15 on its side 124, inserting empty package 17, then insert 142, saline solution containing package 19, then insert 144, and then saline solution containing package 21. Front closure member 150 is then inserted and engaged, and empty package 27 is inserted in open compartment 190. Board-like member 29 with attached tubing is placed in the recess in front of front closure member 150 and closure member 220 is fitted over support member 15.

What is claimed is:

1. A portable container arrangement for use with a blood washing device which comprises
   i. an orthoganally shaped support member formed of corrugated cardboard enclosed at the top, bottom and sides and being open at the front
   ii. a top extension member formed of corrugated cardboard being integral with the top of said support member at its open front and being folded back into said support member to fit tightly therein in a position parallel to the top of said support member, said top extension member having a slit like aperture located at a predetermined distance from the open front of said support member
   iii. a first side extension member formed of corrugated cardboard being integral with a first side of said support member at its open front and being folded back into said support member to fit tightly therein in a position parallel to said first side of said support member, said first side extension member having a slit like aperature located at a predetermined distance from the open front of said support member
   iv. a second side extension member formed of corrugated cardboard being integral with a second side of said support member at its open front and being folded back into said support member to fit tightly therein in a position parallel to said second side of said support member
   v. a bottom extension member formed of corrugated cardboard being integral with the bottom of said support member at its open front and being folded back into said support member to fit tightly therein, said bottom extension member having a folded down end portion and a folded down side portion in contact with the bottom of said support member such that bottom extension member forms a small acute angle with the bottom of said support member
   vi. a removable front closure member formed of corrugated cardboard having vertical front portion having a width which is less than the width of said support member and having a side portion integral therewith and folded into said support member to form a first enclosed compartment in said support member and a second open compartment in said support member which is open at the front of said support member, the side portion of said front closure member having a depth which is less than the depth of said support member and having a bottom edge slanted at said small acute angle formed by said bottom extension member and the bottom of said support member and having folded over integral edge members in contact with said support member such that said removable front closure member fits snugly in said support member and is recessed therein at a predetermined distance, the vertical front portion of said front closure member having integral tabs which engage said slit-like apertures in said top extension member and said side extension member of said support member.
   vii. a pair of removable vertical partitions supported along their lower edges by said bottom extension member and loosely and moveably fitted in said first enclosed compartment in said support member and arranged to form three vertically extending sections in said enclosed compartment
   viii. a first collapsible empty fluid container for collecting waste liquid in one of said three sections
   ix. a pair of collapsible saline solution containers in each of the other of said three sections
   x. and a second collapsible empty fluid container in said open compartment in said support member

* * * * *

UNITED STATES PATENT OFFICE
CERTIFICATE OF CORRECTION

Patent No. 4,043,501  Dated August 23, 1977

Inventor(s) E.W. Larrabee, et al.

It is certified that error appears in the above-identified patent and that said Letters Patent are hereby corrected as shown below:

Column 3, line 65 change "adjointly" to ---adjacently---.

Signed and Sealed this

Twenty-eighth Day of March 1978

[SEAL]

Attest:

RUTH C. MASON
Attesting Officer

LUTRELLE F. PARKER
Acting Commissioner of Patents and Trademarks